(12) United States Patent
Allen

(10) Patent No.: US 6,189,149 B1
(45) Date of Patent: Feb. 20, 2001

(54) TEMPERATURE CHANGE VEST

(76) Inventor: Jeffrey B. Allen, 9102 Lingrove Rd., Brooksville, FL (US) 34613

( * ) Notice: Under 35 U.S.C. 154(b), the term of this patent shall be extended for 0 days.

(21) Appl. No.: 09/464,125

(22) Filed: Dec. 16, 1999

(51) Int. Cl.$^7$ .................. A41D 1/04; A61F 7/00
(52) U.S. Cl. ...................... 2/102; 2/94; 607/114
(58) Field of Search ................ 2/102, 247, 253, 2/94, 2.5, 461, 462, 81, 69, 85, 93, 108, 458, 243.1; 607/108, 114; 62/259.3

(56) References Cited

U.S. PATENT DOCUMENTS

| | | | |
|---|---|---|---|
| 4,601,067 | | 7/1986 | Buonassissi . |
| 5,072,455 | * | 12/1991 | St. Ours .................. 2/102 |
| 5,146,625 | * | 9/1992 | Steele et al. ............. 2/102 |
| 5,305,471 | * | 4/1994 | Steele et al. ............. 2/102 |
| 5,415,222 | * | 5/1995 | Colvin et al. ............ 2/102 |
| 5,692,238 | * | 12/1997 | Watson .................. 2/102 |
| 5,754,982 | * | 5/1998 | Gainer ................... 2/2.5 |
| 5,755,110 | * | 5/1998 | Silvas ................... 62/259.3 |

* cited by examiner

Primary Examiner—Gloria M. Hale
Assistant Examiner—Tejash Patel
(74) Attorney, Agent, or Firm—Larson & Larson, PA; James E. Larson

(57) ABSTRACT

A temperature change vest is provided for fitting around a person's torso. The vest includes seperate front and back panels which attach to one another at respective shoulder strap portions. Hook and loop material is provided upon the shoulder straps for attaching the panels together and for providing a means of adjustment such that the vest can be worn by a variety of people of different sizes. A plurality of horizontally disposed pockets, having open and closed ends and each defining a separate cavity, are provided along outer layers of the front and back panels. Heat packs, capable of retaining a hot or cold temperature, insert within the pockets. Two pair of fastening straps attached to the back panel engage a single pair of fastening strips disposed upon the front panel and work together along a horizontal plane to fit the vest to the person's torso.

3 Claims, 4 Drawing Sheets

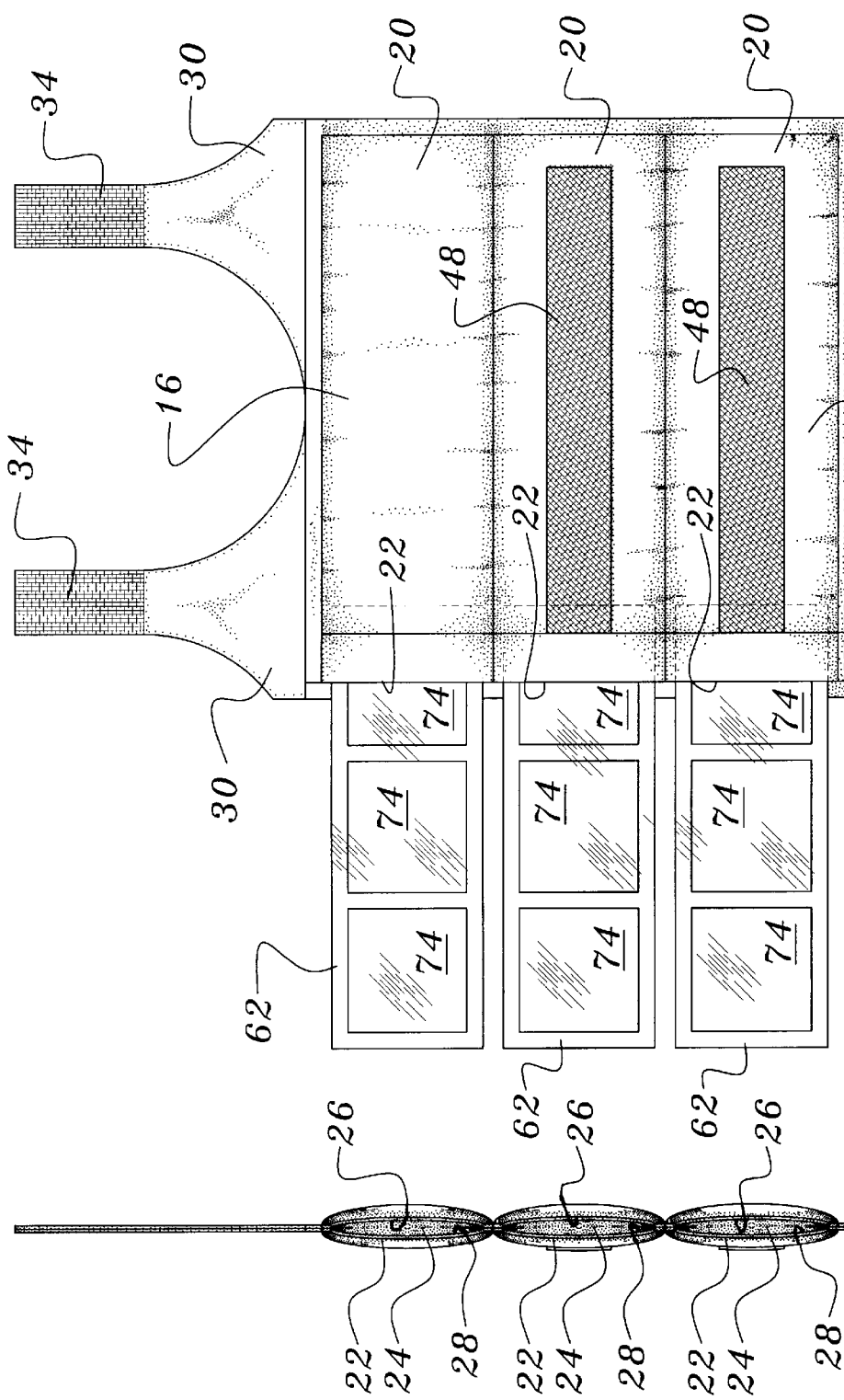

TEMPERATURE CHANGE VEST

BACKGROUND OF THE INVENTION

1. Field of the Invention

This invention relates to a body-worn vest. More particularly, it relates to a body-worn vest capable of affecting a change in the body temperature of the user wearing the vest.

2. Description of Prior Art

Body-worn vests are well known in the prior art and can be used for a variety of purposes. For example, a simple cloth vest is used under the sport jacket of a three-piece suit for aesthetic reasons. Baseball umpires wear vests underneath their shirts to prevent injury from the impact of a high-speed thrown baseball. Law officers wear bullet proof vests to prevent injury or death from a bullet striking the officer's torso. Vest-like structures are also used in scuba-diving (buoyancy compensator) and sky-diving (parachute harness). All of the above mentioned body-worn vests provide a certain function for the user wearing the vest.

Also seen in the prior art are vests used to affect change in the temperature of a body torso. Such can be seen in U.S. Pat. No. 4,601,067 to Buonassissi. The device shown therein includes a pair of front panels (left and right) integrally attached to a back panel, inside pockets extending over inner surfaces of the back panel and inner surfaces of the left and right front panels for receiving hot or cool packs and a plurality of fasteners for fitting the vest upon the user. Although this prior art device can be used to affect change in temperature of a body torso, it has many deficiencies which warrant improvement thereupon. In particular, the vest uses inside pockets for receiving the cool or hot packs. In the case of cool packs, condensation quickly forms as the cool packs begin to melt. This condensation is then felt by the user against his or her body. This results in an uncomfortable wet feeling. There is no means provided in this prior art device for prohibiting the condensation from flowing from the cool packs to the user's body. Further, the inside pockets are disposed in a non-uniform arrangement. For example, two pockets are disposed in the lower portions of the left and right front panels, thereby leaving a great portion of the upper front torso of the user unaffected by the temperature change. As shown in FIG. 2 of the prior art device, four corner pockets are disposed leaving a large column-like portion unaffected along the back side of the user's torso.

The prior art device also relies on a single piece of material to form the back and pair of front panels. Accordingly, the device must be manufactured in various sizes to provide a vest which can fit a variety of different sized users. This results in waste.

An improved vest is needed which can affect a change in temperature of a body torso yet overcome the deficiencies seen in the prior art. In particular, an improved vest should provide for more uniform placement of the cool and hot packs. Such improved vest should also provide a means for adjusting the size of the vest providing a "one size fits all" garment. Further, the improved vest should prohibit any condensation from flowing from the packs to the body of the user wearing the vest.

SUMMARY OF THE INVENTION

I have invented an improved temperature change vest which is worn around the torso of a user. My vest overcomes the deficiencies seen in the prior art, some of which have been described directly hereinabove.

As a first example, my improved vest provides a means for adjusting the size of the vest. This is accomplished by providing separately formed front and back panels which are affixed to one another by a fastener means, preferably along a top portion of each panel. Accordingly, it is first object of the present invention to provide a single adjustable temperature change vest which can be used by a variety of different sized users.

As a second example of improvement, my vest provides for a more uniformed placement of the cool or hot packs thereby covering the entire front and back portion of the user's torso. In particular, a plurality of parallel disposed pockets are provided along an axis parallel to a ground surface. It is therefore a further object of the present invention, to provide an improved temperature change vest having uniformly disposed cool and hot pack pockets.

As a third example of improvement, although not necessarily a last example of improvement, my improved vest employs numerous layers of material around each pocket thereby providing certain advantages over the prior art devices—such layer arrangement not disclosed, taught or suggested anywhere in the prior art. Accordingly, it is yet a further object of the present invention to provide an improved temperature change vest wherein a novel material layer arrangement is employed thereby eliminating "sweating" of the vest and loss of cooling or heating capabilities of the packs, while simultaneously providing a comfortable garment to wear.

BRIEF DESCRIPTION OF THE DRAWINGS

The invention may be best understood by those having ordinary skill in the art by reference to the following detailed description when considered in conjunction with the accompanying drawings in which:

FIG. 2 is a front view of a front panel of the vest of the present invention;

FIG. 3 is a right side view of the front panel of the vest of the present invention;

DETAILED DESCRIPTION OF THE INVENTION

Figure 1:
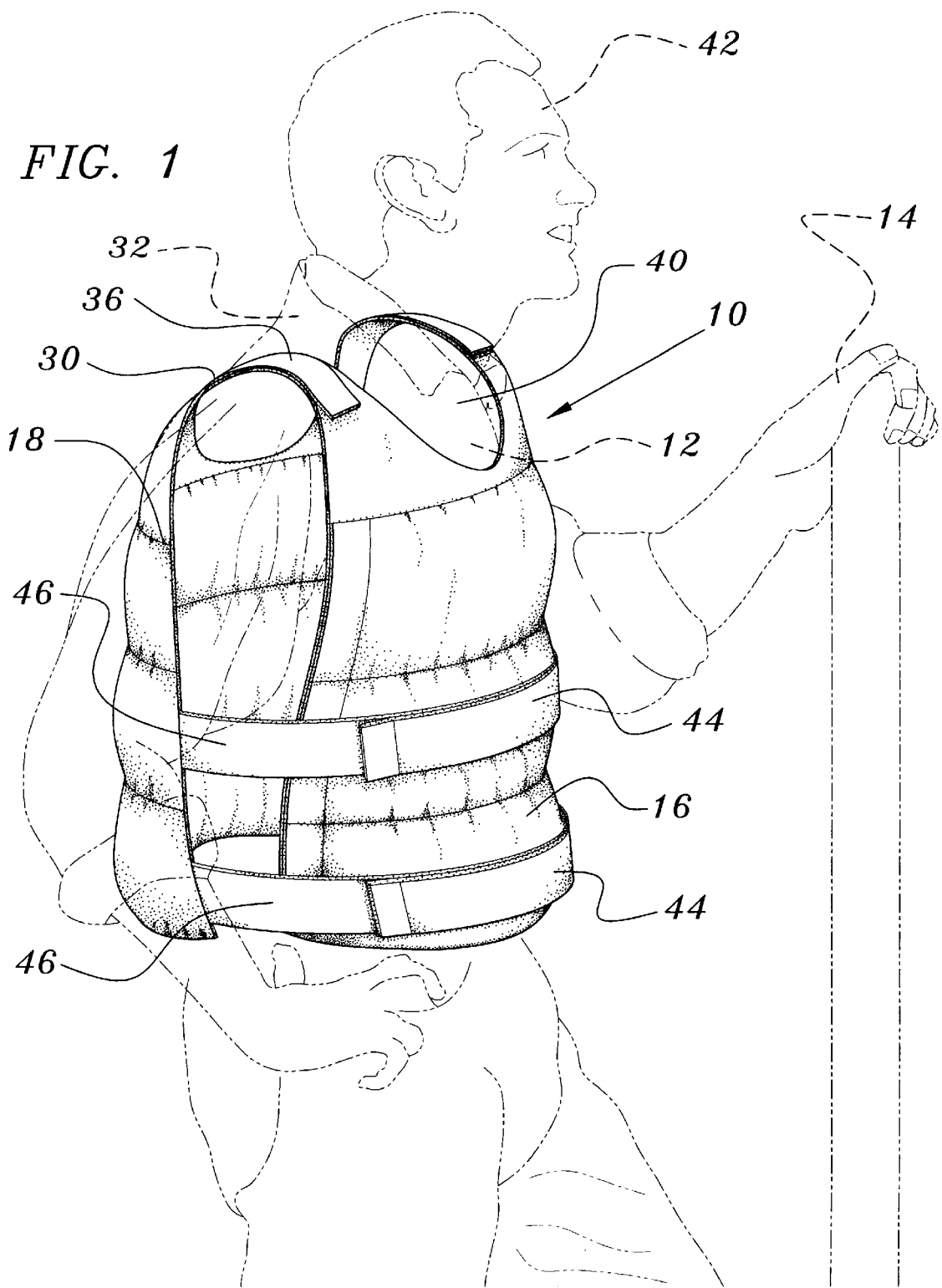
FIG. 1 is a perspective view a temperature change vest of the present invention illustrating how the vest is worn by a user.

Throughout the following detailed description, the same reference numerals refer to the same elements in all figures.

With reference to FIG. 1, a temperature change vest 10 of the present invention is shown on a torso 12 of an individual 14. Vest 10 has a front and back panel portion, 16 and 18 respectively. As shown in FIG. 2, front panel 16 has a plurality of parallel disposed pockets 20. In the preferred embodiment, three pockets 20 are employed. As shown in FIG. 3, each pocket 20 has an opening 22 which provides access to a cavity 24. Each cavity 24 includes a first and second inner wall 26 and 28 which are preferably constructed of a different material. As shown in FIG. 2, each pocket 20 is permanently attached to front panel 16; in the preferred embodiment each pocket 20 is sewn to front panel 16. This of course does not suggest that pockets 20 could not be removably attached by a fastening means, such as hook and loop material (i.e., Velcro®). In fact, such construction could provide a means for adjusting the amount of cooling or heating and also provide a means for lessening the weight of vest 10 by removing un-needed pockets 20.

With continuing reference to FIG. 2, front panel 16 includes a first pair of upwardly extending, generally triangular-shaped shoulder straps 30. Shoulder straps 30 lay upon a shoulder portion 32 of the individual 14 (see FIG. 1) and work in conjunction with reciprocal shoulder straps on back panel 18 (to be discussed hereinafter) providing a means for adjusting the size of vest 10 for variety of different sized users. In this regard, a first portion 34 of a fastening means is provided along the first pair of shoulder straps 30. In the preferred embodiment, hook and loop material is used (i.e., Velcro®) such that first portion 34 of the fastening means is a strip of loop material. Further to the preferred embodiment, a rectangular-shaped strip of loop material is sewn to each of the pair of shoulder straps 30 along a vertical plane.

Figure 4:
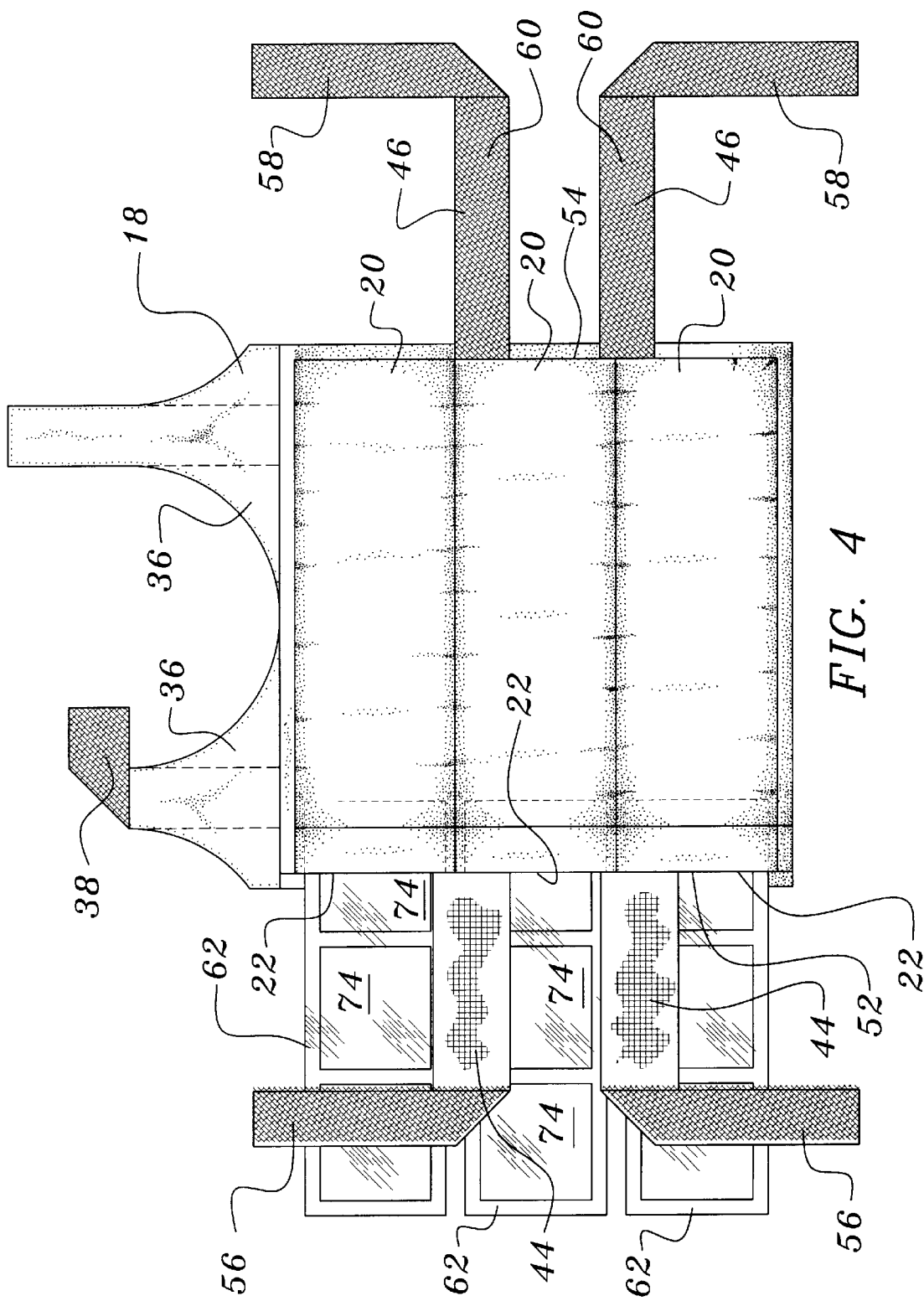
FIG. 4 is a back view of a back panel of the vest of the present invention.

With reference to FIG. 4, back panel 18 is shown. Back panel 18 is similar in structure to front panel 16. For example, a plurality of parallel disposed pockets 20 are provided on back panel 18. In the preferred embodiment, three pockets 20 are employed. Each pocket 20 has an opening 22 which provides access to a cavity 24 (not shown), just as provided on front panel 16. Further, just as with front panel 16, each cavity 24 of each second panel pocket 20 includes a first and second inner wall 26 and 28 which are also preferably constructed of a different material. Each second panel pocket 20 is permanently attached to back panel 18; in the preferred embodiment each pocket 20 is sewn to front panel 16. Again, this does not suggest that pockets 20 could not be removably attached. In such alternate embodiment, pockets 20 are attached by fastening means such as hook and loop material (i.e., Velcro®).

With continuing reference to FIG. 4, back panel 18 includes a second pair of upwardly extending, generally triangular-shaped shoulder straps 36. Shoulder straps 36 also lay upon the shoulder portion 32 of the individual 14 (see FIG. 1) and as stated before, work in conjunction with the first pair of shoulder straps 30 on front panel 16 providing a means for adjusting the size of vest 10 for variety of different sized users. A second portion 38 of the fastening means is provided along the second pair of shoulder straps 36. Since the preferred embodiment utilizes hook and loop material, and loop material is employed as the first portion 34 of the fastening means on the first pair of shoulder straps 30, the second portion 38 of the fastening means is a strip of hook material provided along the second pair of shoulder straps 36 of back panel 18. In the preferred embodiment, a rectangular-shaped strip of hook material is sewn to each shoulder strap 36 along a vertical plane. Referring to FIG. 1, the strips of hook and loop material mate with one another thereby binding front and back panels 16 and 18 together. With the two panels affixed to one another, an opening 40 is provided for permitting the head 42 of the individual 14 to extend through.

With reference to FIG. 1, it is shown that vest 10 can be securely wrapped around the torso 12 of individual 14. This is accomplished through the use of a first and second pair of fastening straps, 44 and 46 respectively, attached to back panel 18 (see FIG. 4) and a single pair of fastening strips 48 mounted to front panel 16 (see FIG. 3). In the preferred embodiment, fastening straps 44 and 46 and fastening strips 48 utilize hook and loop material (i.e., Velcro®) as a fastening means.

Referring to FIG. 2, it is shown that the single pair of fastening strips 48 are mounted to an outer (or first) layer 50 of front panel 16 along a horizontal plane. In the preferred embodiment, wherein three pockets 20 are employed, the single pair of fastening strips 48 are sewn to outer layer 50 along a middle and lower pocket. Loop material is provided thereupon.

Referring to FIG. 4, it is shown that the first and second pair of fastening straps, 44 and 46 respectively, are attached to back panel 18 along opposing side edges, 52 and 54 respectively. Further to the preferred embodiment, the first and second pair of fastening straps, 44 and 46, are positioned to be axially aligned with the single pair of fastening strips 48 located on front panel 16. The first pair of fastening straps 44 employ hook material upon a first side 56, whereas the second pair of fastening straps 46 employ hook material on a first side 58 and loop material on a second side 60. With this arrangement, vest 10 is secured to the individual 14 in the following manner: (1) place vest 10 on individual 14 such that front panel 16 is juxtaposed to a front side of individual 14; (2) engage the loop material along first side 58 of the second pair of fastening straps 46 attached to back panel 18 to the hook material along the single pair of fastening strips 48 located on front panel 16; and (3) engage the loop material along first side 56 of the first pair of fastening straps 44 attached to back panel 18 to the hook material along second side 60 of the second pair of fastening straps 46 attached to back panel 18 and mated with the single pair fastening strips 48. The size adjustment can be made prior to or after engaging the fastening straps, 44 and 46, to the fastening strips 48. However, in a preferred manner, individual 14 would first adjust shoulder straps 30 of front panel 16 and shoulder straps 36 of back panel 18 to set vest 10 to its proper sized position.

Referring to FIGS. 2 and 4, it is shown that cavities 24 are formed to receive a heating pack 62. Heating pack 62 can be either a cool pack or hot pack, depending on the change of temperature the user wishes to manipulate. In its preferred form, each heating pack 62 includes three sealed compartments 74 containing a substance capable of being frozen or heated and which is known to not surrender its heat quickly (i.e., if frozen—slow to thaw; if heated—slow to cool off). In the preferred embodiment, a polymer based material 76 is used. Referring to FIG. 3, it shown that openings 22 can be shut by a closure means, including, but not limited to, hook and loop material (the preferred closure means), a zipper and a snap button.

Figure 5:
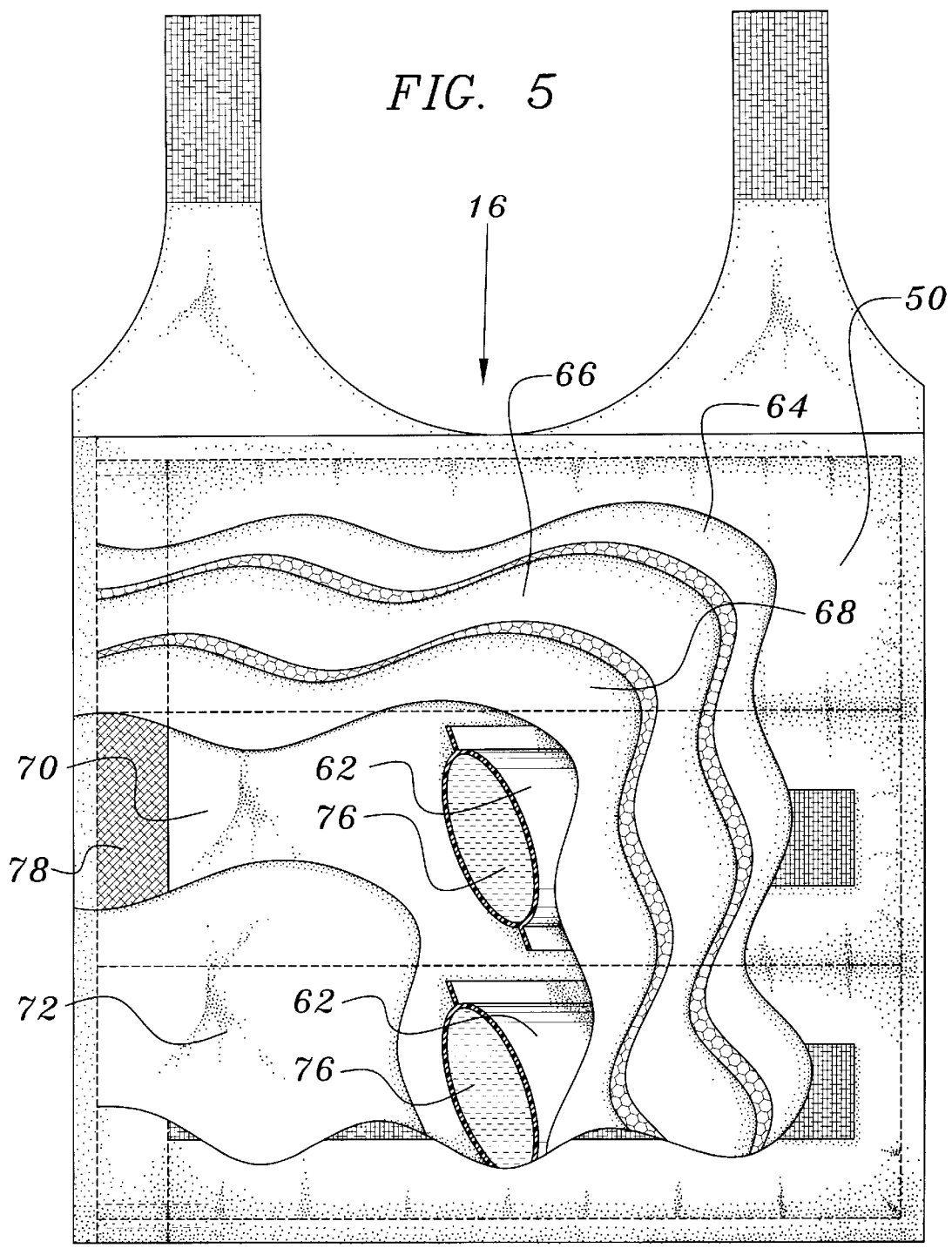
FIG. 5 is a front view, partially in section, of the front panel of the vest of the present invention.

Vest 10 utilizes a novel combination of material layers to overcome deficiencies seen in the prior art. As shown in FIG. 5, both front and back panels, 16 and 18, employ a six material layer combination. Outer layer (or first layer) 50 is made of a tightly woven nylon, such as 500 Denier Cordura®. A second layer 64 is made of an insulating material, such as Thinsulate™ Type CS 100. A third layer 66 is also made of an insulating material, such as Thinsulate™ Type CS 200. Two insulating layers are employed to provide extra insulating properties. A fourth layer 68 (also considered the second inner wall 28 of cavity 24) is made of a material such as Ultrex® —2 Ply. A fifth layer 70 (also considered the first inner wall 26 of cavity 24) is made of a tightly woven nylon, such as 500 Denier Cordura®. A sixth and final inner layer 72 (that which makes contact with the user's body) is made of a flexible nylon mesh. Heating packs 62 insert between the fourth and fifth layers, 68 and 70 respectively.

Equivalent elements can be substituted for the ones set forth above such that they perform the same function in the same way for achieving the same result.

Having thus described the invention what is claimed and desired to be secured by Letters Patent is:

1. A temperature change vest for employment over a head and upon a torso of a person, the vest comprising:
   a) a six layered front panel having a first generally rectangular-shaped body portion and a first pair of integrally attached upwardly extending shoulder straps located at an upper end of the first body portion,
   b) a six layered back panel having a second generally rectangular-shaped body portion and a second pair of integrally attached upwardly extending shoulder straps located at an upper end of the second body portion,
   c) a plurality of horizontally disposed outer pockets attached to the front and back panels along the first and second body portions, each pocket having an open and closed end and defining separate inner cavities,
   d) a plurality of heat packs inserted within the plurality of outer pocket cavities, each heat pack capable of being frozen or heated,
   e) securing means for attaching the front panel to the back panel disposed upon the first and second pair of shoulder straps, the securing means defining an opening in which the person's head can extend through,
   f) fastening means for fitting the vest to the person's torso disposed upon the front and back panels and
   g) both the six layered front and back panels having a first layer of a tightly woven nylon, a second layer of a first insulator, a third layer of a second insulator, a fourth layer of a moisture prohibitor, a fifth layer of a tightly woven nylon and a sixth layer of a nvlon mesh lining.

2. A temperature change vest for employment over a head and upon a torso of a person, the vest comprising:
   a) a six layered front panel having a first generally rectangular-shaped body portion, a first pair of integrally attached upwardly extending shoulder straps located at an upper end of the first body portion and a first set of three horizontally disposed outer pockets, each pocket having an open and closed end and defining separate inner cavities,
   b) a six layered back panel having a second generally rectangular-shaped body portion, a second pair of integrally attached upwardly extending shoulder straps located at an upper end of the second body portion and a second set of three horizontally disposed outer pockets, each pocket having an open and closed end and defining separate inner cavities,
   c) six heat packs, one each inserted within the first and second set of outer pocket cavities, each heat pack capable of being frozen or heated,
   d) a strip of loop material attached along a vertical plane of each of the first pair of front panel shoulder straps,
   e) a strip of hook material attached along a vertical plane of each of the second pair of back panel shoulder straps,
   f) fastening means for fitting the vest to the person's torso disposed upon the front and back panels and
   g) both the six layered front and back panels having a first layer of a tightly woven nylon, a second layer of a first insulator, a third layer of a second insulator, a fourth layer of a moisture prohibitor, a fifth layer of a tightly woven nylon and a sixth layer of a nylon mesh lining.

3. The temperature change vest of claim 2, wherein the fifth layer is a first inner wall of each of the cavities and the fourth layer is a second inner wall of each of the cavities.

* * * * *